US006354989B1

United States Patent
Nudeshima

(10) Patent No.: US 6,354,989 B1
(45) Date of Patent: Mar. 12, 2002

(54) RADIATION SOURCE DELIVERY WIRE AND CATHETER ASSEMBLY FOR RADIATION THERAPY PROVIDED WITH THE SAME

(75) Inventor: Masahiro Nudeshima, Tokyo (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/416,938

(22) Filed: Oct. 13, 1999

(30) Foreign Application Priority Data

Oct. 14, 1998 (JP) .......................................... 10-292084
Oct. 27, 1998 (JP) .......................................... 10-306005

(51) Int. Cl.[7] .......................... A61N 5/00; A61M 36/00
(52) U.S. Cl. .............................................. 600/3; 600/7
(58) Field of Search ............................. 250/106; 600/3, 600/7; 604/264; 606/198

(56) References Cited

U.S. PATENT DOCUMENTS

| 3,655,984 | A | * | 4/1972 | Dukes ........................ 250/106 |
| 5,106,360 | A | * | 4/1992 | Ishiwara et al. ................ 600/2 |
| 5,199,939 | A | | 4/1993 | Dake et al. |
| 5,342,283 | A | | 8/1994 | Good |
| 5,354,257 | A | | 10/1994 | Roubin et al. |
| 5,503,613 | A | | 4/1996 | Weinberger |
| 5,503,614 | A | | 4/1996 | Liprie |
| 5,556,389 | A | * | 9/1996 | Liprie ........................ 604/264 |
| 5,624,372 | A | | 4/1997 | Liprie |
| 5,728,042 | A | | 3/1998 | Schwager |
| 5,766,204 | A | * | 6/1998 | Porter et al. ................. 606/198 |
| 5,772,642 | A | | 6/1998 | Ciamacco, Jr. et al. |
| 5,833,593 | A | * | 11/1998 | Liprie ............................ 600/3 |
| 5,928,130 | A | * | 7/1999 | Schmidt ......................... 600/7 |

FOREIGN PATENT DOCUMENTS

| EP | 0 497 495 A2 | 8/1992 |
| EP | 95109741 | 6/1995 |
| EP | 95109741.9 | 6/1995 |
| EP | 0 778 051 A1 | 6/1997 |
| JP | 4-309368 | 10/1992 |
| JP | 9-10337 | 1/1997 |
| JP | 9-508038 | 8/1997 |
| WO | 94/25106 | 11/1994 |
| WO | WO 97/18012 | 5/1997 |
| WO | WO 97/19706 | 6/1997 |
| WO | WO 99/15234 | 4/1999 |

* cited by examiner

*Primary Examiner*—Eric F. Winakur
*Assistant Examiner*—Nikita Veniaminov
(74) *Attorney, Agent, or Firm*—Burns, Doane, Swecker & Mathis, LLP

(57) ABSTRACT

A radiation source delivery wire has a flexible operating wire member, and an irradiation member including a radiation source for applying radiation to a target portion in a cavity of a living body. The irradiation member including the radiation source is so constructed as to be flexibly bendable, and a distal end portion of the operating wire member constitutes a narrowing portion which gradually narrows toward its distal end.

41 Claims, 6 Drawing Sheets

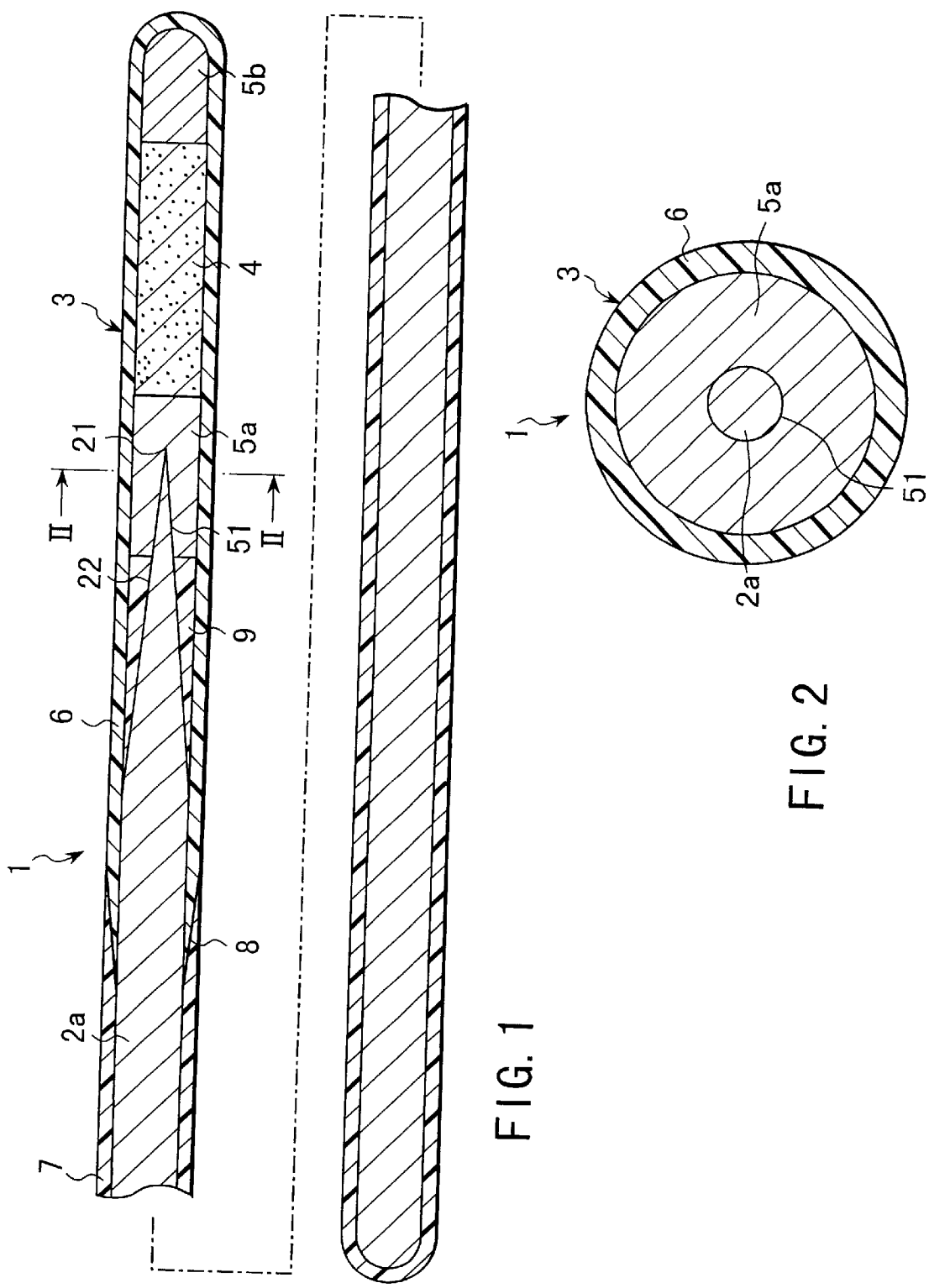

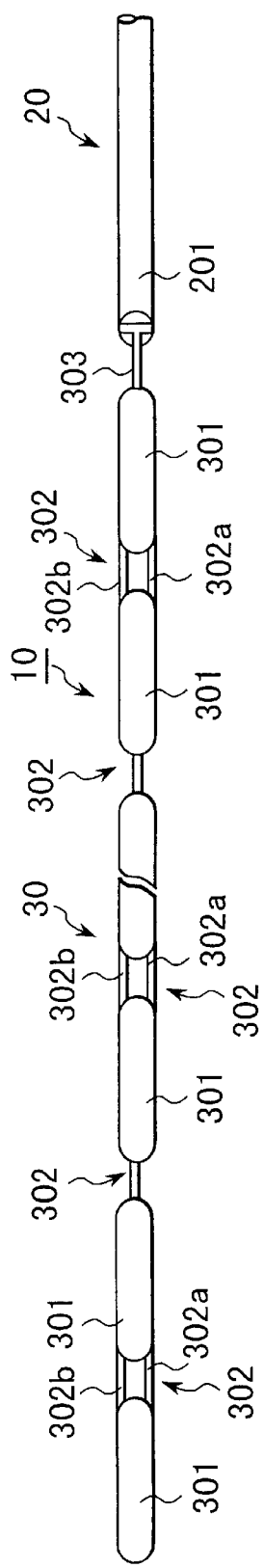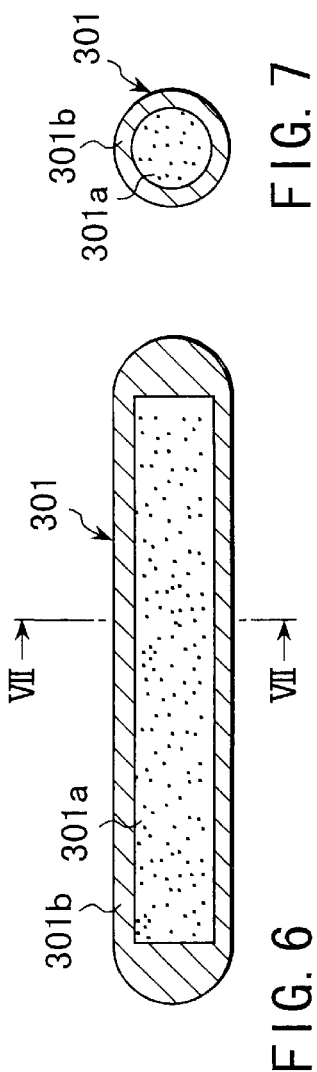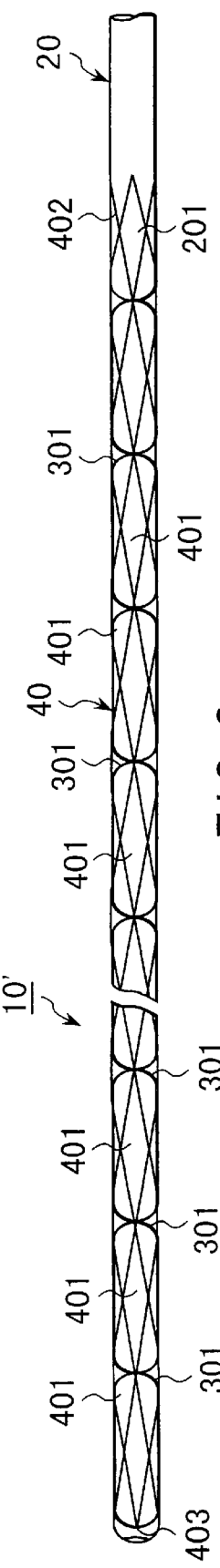

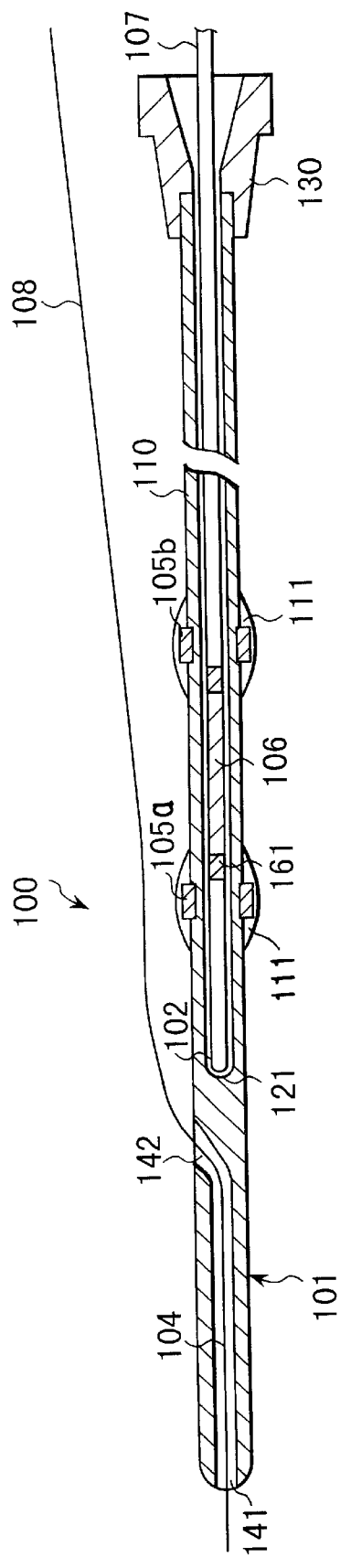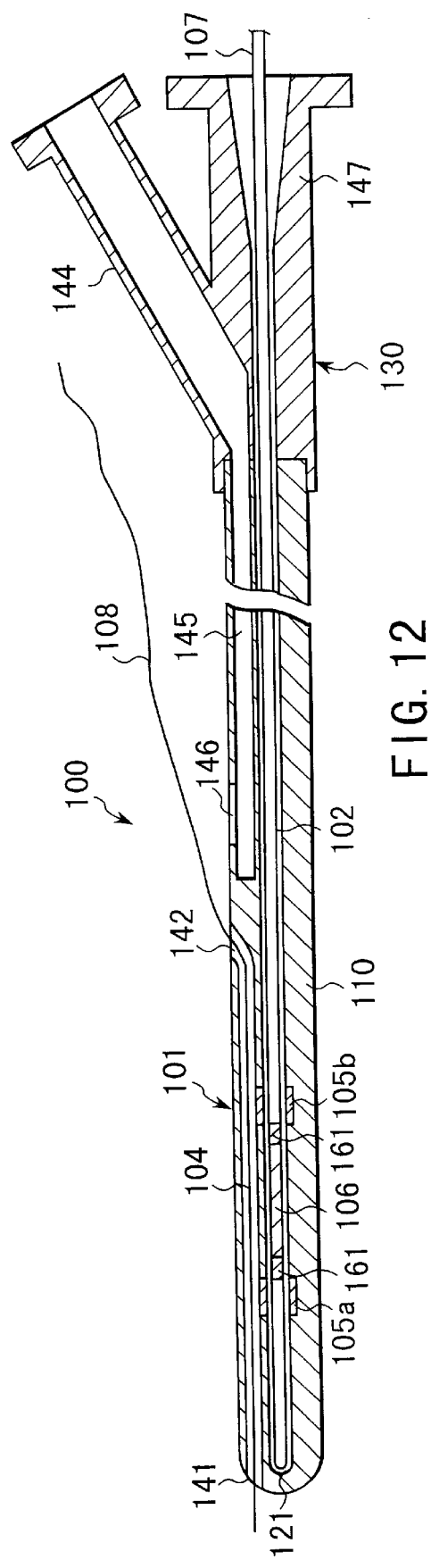
FIG. 11
FIG. 12

RADIATION SOURCE DELIVERY WIRE AND CATHETER ASSEMBLY FOR RADIATION THERAPY PROVIDED WITH THE SAME

BACKGROUND OF THE INVENTION

The present invention relates to a radiation source delivery wire for use in radiation therapy, mainly, in a cavity in the living body such as the blood vessel and a catheter assembly for radiation therapy, provided with the same.

Radiation therapy is a medical treatment by applying radiation source to a lesion tissue or the like. Recently, to intensify its treatment effect while reducing a side effect, a method has been employed in which a radiation source is placed just in the vicinity of the morbid tissue. For example, the radiation therapy is carried out to prevent a restenosis after percutaneous transluminal coronary angioplasty (PTCA) is carried out for coronary artery stenosis. In the radiation therapy, mainly a catheter or wire is used as a means for delivering the radiation source.

The radiation therapy includes, for example, inserting a catheter into a cavity of a patient, dwelling a distal end thereof in the vicinity of a target tissue, sending a radiation source delivery wire into the catheter with a predetermined method to position the radiation source near a target portion and dwelling it in the living body for a predetermined time so as to apply the radiation.

U.S. Pat. No. 5,728,042 discloses an example of the radiation therapy wire. It includes a core wire, wire coil (radiation source) made of radioactive substance. wound up around the core wire and radiopaque coils provided on the distal and proximal ends of the radiation source. Because this radiation therapy wire has radiopaque coils, a position of the radiation source can be detected. However, because the radiation source is composed of wire coil made of radioactive material, a size of the wire is relatively large and smoothness of the surface thereof is lost, so that when inserted into or removed from the catheter or lumen, the catheter or tissue may be damaged. A more important problem is that the flexibility of the entire radiation therapy wire is insufficient so that it is difficult to ensure the operability and safety of the catheter.

When the target tissue is located in a tortuous cavity or at a terminal of a branched cavity, if the flexibility of the wire for delivering the radiation source to the target portion is insufficient, operation of the wire and positioning of the radiation source become difficult.

BRIEF SUMMARY OF THE INVENTION

Accordingly, it is an object of the present invention to provide a radiation source delivery wire wherein flexibility of a distal end portion thereof is improved and operability and safety can be secured when inserted into a cavity of a living body even if a target tissue is located in a tortuous cavity or at a terminal of a branched cavity, as well as a catheter assembly for radiation therapy provided with such a radiation source delivery wire.

Another object of the present invention is to provide a radiation source delivery wire whose radiation source position can be identified accurately so as to appropriately apply the radiation to the target tissue so that a bad influence upon the living body can be suppressed, thereby improving a treatment effect, as well as a catheter assembly for radiation therapy, provided with such a radiation source delivery wire.

To achieve the above objects, the present invention provides a radiation source delivery wire comprising: a flexible operating wire member; and an irradiation member including a radiation source for applying radiation to a target portion in a cavity of a living body, wherein the irradiation member including the radiation source is so constructed as to be flexibly bendable, and a distal end portion of the operating wire member constitutes a narrowing portion which gradually narrows toward its distal end.

Further, the present invention provides a radiation source delivery wire comprising: a flexible operating wire member; an irradiation member having a radiation source comprising powdery emitting member for applying radiation to a target portion in a cavity of a living body; and a thin-walled, flexible tube accommodating the irradiation member.

Still further, the present invention provides a radiation source delivery wire comprising: a flexible operating wire member; and an irradiation member comprising a flexible, deformable medium and a radioactive substance mixed in or carried by the medium, for applying radiation to a target portion in a cavity of a living body.

Still further, the present invention provides a radiation source delivery wire comprising: a flexible operating wire member; and an irradiation member for applying radiation to a target portion in a cavity of a living body, wherein the irradiation member includes a connected body comprising a plurality of individual radiation sources and flexibly bendable connectors connecting the plurality of individual radiation sources substantially on a common axial line, and a joint portion joining a proximal end of the connected body to a distal end of the operating wire member, and the connected body is provided on distal end side relative to the distal end of the operating wire member.

According to another aspect of the present invention, there is provided a catheter assembly for radiation therapy comprising: (a) a radiation source delivery wire of the present invention; and (b) a catheter for radiation therapy comprising a catheter body and an elongated lumen which is provided in the catheter body and through which the radiation source delivery wire can be inserted.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

FIG. 1 is a longitudinal sectional view showing a radiation source delivery wire according to a first embodiment of the present invention;

FIG. 2 is a sectional view taken along the line II—II of FIG. 1;

FIG. 5 is a side view showing a radiation source delivery wire according to a third embodiment of the present invention;

FIG. 6 is a longitudinal sectional view showing an individual radiation source used in the present invention;

FIG. 7 is a sectional view taken along the line VII—VII of FIG. 6;

FIG. 8 is a side view showing a radiation source delivery wire according to a fourth embodiment of the present invention;

FIG. 11 is a longitudinal sectional view showing a first embodiment of a catheter assembly for radiation therapy of the present invention;

FIG. 12 is a longitudinal sectional view showing the second embodiment of a catheter assembly for radiation therapy of the present invention;

DETAILED DESCRIPTION OF THE INVENTION

Figure 3:
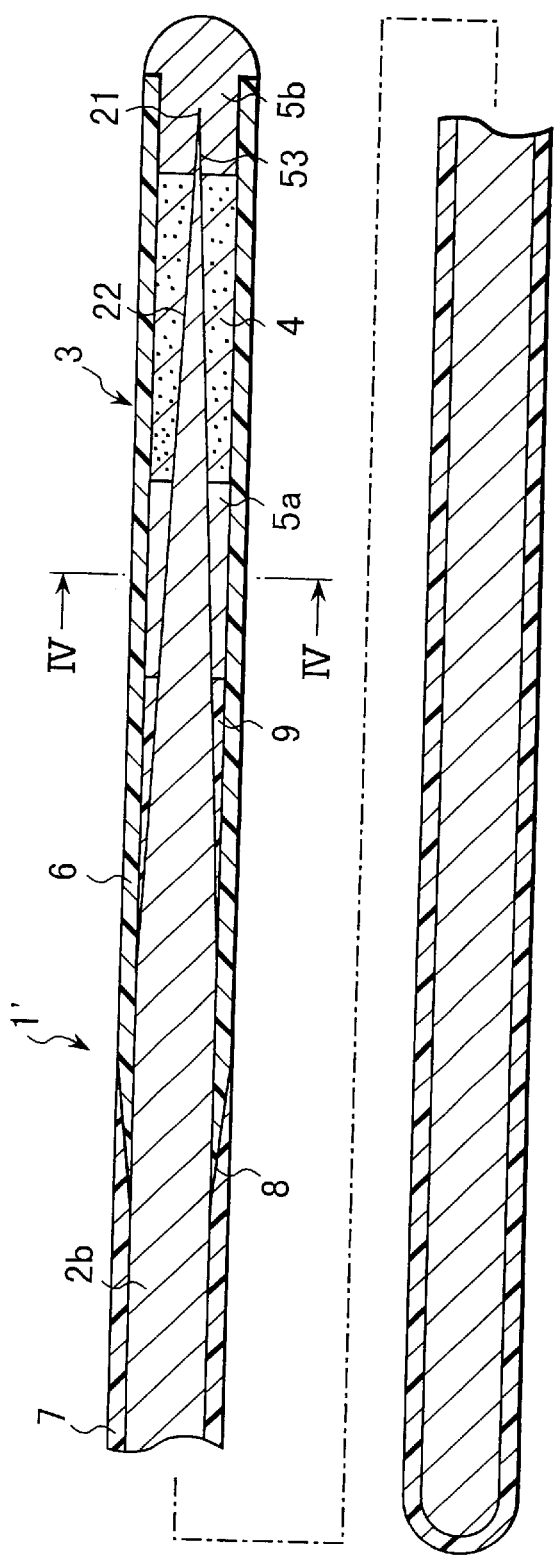
FIG. 3 is a longitudinal sectional view showing a radiation source delivery wire according to a second embodiment of the present invention.

A radiation source delivery wire of the present invention comprises a flexible operating wire member and an irradiation member including a radiation source. The irradiation member of the present invention is so constructed as to be deformable such that it is capable of following a deformation or bending of a catheter tube inserted following a tortuous or branched cavity of a living body or patient, and is capable of following such a tortuous or branched cavity, even if a target tissue is located in such a tortuous cavity or at a terminal end of such a branched cavity.

Hereinafter, the present invention will be described in detail with reference to the accompanying drawings. Throughout all the FIGURES, like reference numerals denote the like parts or components. Meanwhile, "distal" and "proximal" used in this specification are based on an insertion direction into a cavity of a living body.

FIG. 1 is a longitudinal sectional view showing a first embodiment of a radiation source delivery wire of the present invention and FIG. 2 is a sectional view taken along the line II—II of FIG. 2.

As shown in FIGS. 1 and 2, the radiation source delivery wire 1 according to the first embodiment of the present invention comprises a flexible operating wire member 2a and an irradiation member 3 for emitting radiation to a target portion in a cavity of a living body.

The operating wire member 2a is composed of fine linear body and functions to transmit an operation at the proximal end thereof to the distal end. Therefore, the operating wire member 2a is preferably composed of a material having appropriate stiffness and flexibility. Such a material includes, for example, metallic material such as stainless steel or tungsten, superelastic alloy such as Ni—Ti alloy, Cu—Al—Ni alloy, Cu—Zn—Al alloy or Fe—Mn alloy, polyamide, polyimide, ultra-high-molecular weight polyethylene, carbon fiber, and glass fiber, and particularly superelastic alloy is most preferable. The operating wire member 2a made of the superelastic alloy has appropriate pliability, elasticity, sliding performance, mechanical strength, trackability, anti-kink performance and the like, and the radiation source delivery wire 1 made of such an operating wire member 2a has excellent operability and handling performance when it is inserted through the catheter and cavity up to the vicinity of a target tissue.

Further, the operating wire member 2a which is made of stranded cable formed by stranding a plurality of wires is also preferable. If the operating wire member 2a is composed of the stranded wire, the anti-kink performance and tensile strength are improved so that a function for transmitting an operation at the proximal end to a distal end of the operating wire member 2a can be exerted fully.

As shown in FIG. 1, preferably, a distal end portion of the operating wire member 2a is a narrowing portion 22 whose diameter is gradually reduced toward a distal end 21 thereof. This narrowing portion 22 improves pliability and flexibility of the distal end of the radiation source delivery wire 1. Thus, the radiation source delivery wire 1 can be brought to a target tissue through bent portion, loop portion, branched portion and the like in the catheter and the cavity. At that time, the tissue may not be damaged by a distal end of the radiation source delivery wire 1.

Further, the narrowing portion 22 is desirably constructed such that a diameter thereof is gradually reduced symmetrically relative to the axis of the operating wire member 2a. Consequently, the operating wire member 2a indicates an equal bending performance in every direction, thereby improving operability and safety.

An external surface of the operating wire member 2a is provided with a covering layer 7 almost through the entire length excluding the narrowing portion 22. The covering layer 7 provides the surface of the operating wire member 2a with resilience and pliability and further improves lubricity when it is inserted into or pulled out of the catheter or lumen.

Material of the covering layer 7 includes, for example, a thermoplastic resin including polyolefin such as polyethylene or polypropylene, polyester such as ethylene-vinyl acetate copolymer, polyethylene terephthalate or polybutylene terephthalate, polyvinyl chloride, polyamide, polyimide, polyurethane, and fluororesin, as well as elastomer and copolymer thereof, polymer alloy, various kinds of rubbers such as silicone rubber or fluororubber, and combinations of two or more thereof.

The covering layer 7 may be formed using any of these materials according to dipping method, hot melting coating, spray method, heat shrinkage tube or the like.

The radiation source delivery wire 1 has the irradiation member 3 at a distal end thereof. The irradiation member 3 comprises a radiation source 4 and radiopaque markers 5a and 5b.

The radiation source 4 comprises radioactive substance for emitting radiation to the target portion in the cavity. As the radioactive substance, a material can be used which contains clinically usable radio-isotope, for example, phosphorus-32, calcium-45, cobalt-60, strontium-90, yttrium-90, ruthenium-106, xenon-103, rhenium-188, rhodium-106, iridium-192, gold-198, tungsten-188. Of these, a radioactive substance containing radio-isotope which emits β-rays is preferable.

Because the γ ray which is used for radiation therapy since before has a strong penetration force, from the living body surface up to deep organ may be exposed thereto by irradiation. Further, because it is scattered in the living body so that it may damage normal cells seriously, a radiation source having a small activity must be used, and therefore, treatment time is extended. Further, because there is a problem that an operator may be exposed to the radiation, remote control system using an expensive after-loader must be used, so that a problem may be generated in operability.

To the contrary, because the β-ray has a weak penetration force in the living body, the scattering thereof is small so that it is capable of inhibiting only hyperplasia tissue locally. Therefore, this ensures excellent handling performance and safety performance, thereby preventing an exposure of the operator and improving treatment effect. Further, because the penetration force of the β-ray is not so strong as the γ ray, the β-ray is easy to shield from, so that protection of the operator from the radiation can be carried out easily. Further, the β-emitting source 4 can be accommodated in a resin tube 6 (described in detail below) easily so as to form the radiation source delivery wire 1. Therefore, a radiation source which does not substantially emit γ ray, but emits β-ray is preferable.

A configuration and shape of the radiation source 4 are not restricted to any particular ones, but it only has to be so structured to be entirely flexible and bendable. For example, although it may be constructed in the form of a rod, tube, coil, wire mesh or the like, preferably, it is composed of a powdery radiator or emitting member. The radiation source composed of powdery emitting member can change in its shape freely following a bending of the radiation source delivery wire 1 so that it is capable of following a motion of the radiation source delivery wire 1.

The powdery radiator or emitting member can be obtained by carrying the aforementioned radioactive substance on a granular carrier. For example, the powdery radiator may be obtained by dissolving the radioactive substance in acid solution so as to impregnate porous particles such as glass, ceramics with the solution or dispersing powder of the radioactive substance in a resin material and granulating the resin material.

Further, in addition to the powder, a radiator or emitting member may be obtained by mixing a radioactive substance into a flexible, bendable medium. The medium may be any material provided it is soft and can be readily deformed by an external force, and includes, for example, a rubber material such as a silicone rubber, a flexible resin material such as a thermoplastic elastomer or a soft polyurethane, and water adsorptive gel such as polyvinyl alcohol. Such a radiator or emitting member may be obtained by dispersing powder of the radioactive substance in the soft rubber material such as silicone rubber, or the soft resin material such as a thermoplastic elastomer. Alternatively, the radiator can be obtained by impregnating a porous member made of these materials with a solution of the radioactive substance. The radiation source made of such a flexible, bendable medium carrying or containing the radioactive substance is capable of ensuring an excellent trackability relative to a motion of the radiation source delivery wire 1.

Although the length of the radiation source 4 can be set up appropriately depending on an irradiation portion, irradiation target and the like, preferably it is 5 to 70 mm in viewpoints of handling, safety and the like. The length is more preferably about 10 to 50 mm, and most preferably about 20 to 40 mm.

The radiopaque markers 5a and 5b are located at both ends of the radiation source 4 so as to make it possible to recognize the location or position of the radiation source 4, an irradiation range by the radiation source 4 and the like under (particularly X-ray) fluoroscopy. Further, the radiation source 4 is fixed in the tube 6 by the radiopaque markers 5a, 5b so as to prevent the radiation source 4 from being moved during treatment leading to radiation error or the like. Specifically if the radiation source 4 is powdery, the radiopaque markers 5a, 5b function as a lid so as to enclose the radiation source 4 securely.

The radiopaque markers 5a are 5b are composed of radiopaque material. Therefore, locations of the radiation source delivery wire 1 and radiation source 4 can be visually identified under fluoroscopy. The radiopaque material composing the radiopaque markers 5a, 5b includes for example, heavy metal such as Au, Ag, Pt, W, Pb, alloys mainly containing such a heavy metal, barium sulfate, bismuth oxide, and they can be formed of a resin material with which these radiopaque material is mixed.

Each of the radiopaque markers 5a and 5b is composed of a hollow cylinder whose outer diameter at its distal end is substantially equal to or slightly smaller than a maximum diameter of the operating wire member 2a. A fitting portion 51 capable of fitting to a distal end 21 of the operating wire member 2a is provided at a distal end of the radiopaque marker 5a. On the other hand, a distal end of the radiopaque marker 5b is round. By forming the distal end in a round shape, damage of the tissue and the like can be prevented when the radiation source delivery wire 1 is inserted into or removed from the cavity.

The operating wire member 2a is desirably so constructed as to fit to the fitting portion 51 provided coaxially in the radiopaque marker 5a as shown in FIG. 2. Consequently, a bending stress or the like transmitted from the distal end of the operating wire member 2a can be applied to the irradiation member 3 equally, thereby improving the safety and operability during therapy. In other words, the marker 5a functions as "transmitting member" or "enlarged portion", for transmitting a bending stress or the like to the irradiation member 3, which is arranged between the irradiation member 3 and the wire member 2a and closely contacts the irradiation member 3. The operating wire member 2a and the radiopaque marker 5a can be fixed securely via the fitting portion 51 by bonding with an adhesive or hot melting.

The configuration of the radiopaque marker is not restricted to cylinder, but may be ribbon-like body or linear body.

The irradiation member 3 is accommodated in the tube 6 having a thin, flexible wall, together with the radiopaque markers 5a, 5b, as shown in FIG. 1. Thus, this is different from a structure in which a coil made of radioactive material is attached directly to the operating wire member such that it is exposed outside, and an outer surface of the radiation source delivery wire 1 can be smoothed. The radiation source 4 is sealed completely together with the radiopaque markers 5a, 5b by the tube 6, and is fixed at a predetermined position in the radiation source delivery wire 1.

Such a tube 6 is preferably formed of a flexible resin material. The resin material includes the same materials as used for the covering layer 7. By forming the tube 6 of such a resin material, flexibility and resilience of the distal end portion of the radiation source delivery wire 1 are secured so that it can be advanced smoothly with safety through paths in the catheter and cavity of a living body.

Meanwhile, the tube 6 and covering layer 7 may be formed of the same material or different materials.

Preferably, the tube 6 is directly (without any intervening member) to the irradiation member 3 so as to function as "encapsulating member" encapsulating sealingly the irradiation member 3. Thus, the distal end of the radiation source delivery wire 1 has high flexibility and the manufacturing process can be more simplified.

The distal end portion of the tube 6 is closed. This closed distal end portion is capable of preventing the radiation source 4 and radiopaque markers 5a, 5b accommodated inside the tube 6 from being shifted or slipped out. By sealing at least one end of the tube 6, the sealing performance is intensified, thereby preventing a leakage of the radiation source 4 and securing the safety.

The proximal end of the tube 6 is joined to the covering layer 7 at a joint portion 8 such that a continuous smooth outside surface of the radiation source delivery wire 1 can be formed. The joint portion 8 is formed of an oblique face inclined such that an inside face of a distal portion of the covering layer 7 mates with an outside face of a proximal portion of the tube 6. At the joint portion 8, the covering layer 7 and tube 6 are overlaid along the direction of the diameter and both of them are joined securely by bonding with an adhesive, hot melting, ultrasonic fusion or the like. As a result, the operating wire member 2a and irradiation member 3 are integrated.

The irradiation member 3 is preferably provided at the narrowing portion 22 of the operating wire member 2a. Consequently, the diameter of the radiation source delivery wire 1 can be reduced and the outside surface thereof can be smoothed.

Further, a fixing member 9 is provided so as to fill a space between the tube 6 and narrowing portion 22. As a result, the irradiation member 3 and operating wire member 2a are fixed securely. As the fixing member 9, an adhesive, a resin or the like can be used.

The tube 6 may be provided to cover up to the proximal end of the operating wire member 2a. With such a structure, smoothness of the surface of the radiation source delivery wire 1 can be easily achieved, and because the joint portion 8 is provided, there is no risk that the irradiation member 3 may be detached from the operating wire member 2a.

Although the length of the radiation source delivery wire 1 is set up appropriately depending on a portion which this device is applied to, preferably it is 0.5 to 3 mm, and more preferably, 1.5 to 2.5 mm. Preferably, an outer diameter of the wire 1 is 0.1 to 1.5 mm, and more preferably, 0.25 to 0.9 mm.

To manufacture the radiation source delivery wire 1, for example, the tube 6 is formed by extrusion molding, cut to a predetermined length and its one end is closed in a half-spherical form with a heated molding die to provide a distal end of the radiation source delivery wire. By disposing the radiopaque markers 5b produced preliminarily at the closed end portion of the tube 6 at this time, closing of the tube 6 and fixing of the radiopaque marker 5b are carried out at the same time.

The proximal end of the tube 6 is preferably cut such that a thickness thereof gradually decreases. By so cutting the tube, an area of the joint portion 8 relative to the covering layer 7 can be increased, and thus the joint between the both can be intensified and an outside surface of the joint portion 8 can be smoothed.

Next, the radiation source 4 of a predetermined amount is charged from the proximal end opening of the tube 6. Then, the radiopaque marker 5a to which a distal end portion 21 of the tapered operating wire member 2a has been fit preliminarily is inserted into the proximal end opening of the radiation source 4 and fixed therein. Further, the fixing member 9 of a resin or the like is loaded in a gap between the tube 6 and narrowing portion 22.

Finally, the covering layer 7 is provided on the surface of the operating wire member 2a. At this time, the covering layer 7 is joined to the proximal end of the tube 6 such that they are overlaid along the direction of the diameter. After the joint portion 8 is bonded with an adhesive or hot-melted, the surface of the joint portion 8 is smoothed. In this way, the radiation source delivery wire 1 shown in FIGS. 1 and 2 can be obtained.

Figure 4:
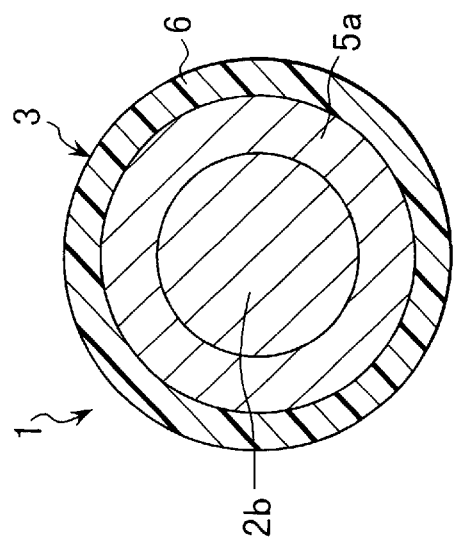
FIG. 4 is a sectional view taken along the line IV—IV of FIG. 3.

FIG. 3 is a longitudinal sectional view showing a radiation source delivery wire according to a second embodiment of the present invention, and FIG. 4 is a sectional view taken along the line IV—IV of FIG. 3. In these FIGURES, like reference numerals denote like components or parts, and a description thereof is omitted.

The radiation source delivery wire 1' of the second embodiment is different from the first embodiment in that the operating wire member 2b penetrates the radiopaque marker 5a and radiation source 4 so that a distal end thereof extends up to the radiopaque marker 5b and a distal end of the tube 6 is closed by the radiopaque marker 5b.

Because the operating wire member 2b of the radiation source delivery wire 1' extends up to a distal end thereof, transmission of pushing force and torque force applied to the irradiation member 3 located at the distal end portion of the radiation source delivery wire 1' is improved, providing improved operability.

Preferably, the operating wire member 2b is so constructed to fit to the fitting portion 53 provided in the center of the radiopaque marker 5b. Preferably, the operating wire member 2b penetrates the center of the radiopaque marker 5b and the center of the radiation source 4 as shown in FIG. 4. Consequently, as in the first embodiment, a bending stress and the like transmitted from the proximal end portion of the operating wire member 2b can be applied equally to the irradiation member 3, providing improved safety and operability during therapy. In other words, the marker 5a functions as "transmitting member" or "enlarged portion", for transmitting a bending stress or the like to the irradiation member 3, which is arranged between the irradiation member 3 and the wire member 2b and closely contacts the irradiation member 3.

The distal end opening of the tube 6 is closed by the radiopaque marker 5b. By closing the distal end of the tube 6 by the radiopaque marker 5b, the radiation source 4 can be loaded from the distal end. Thus, the assembly and installation of the irradiation member 3 can be carried out further simply.

The tube 6 and radiopaque marker 5b can be fixed by any suitable method, including bonding with an adhesive bonding or hot-melting of the both, after the radiopaque marker 5b is fit to the tube 6.

Because the narrowing portion 22 constitutes the distal end portion of the operating wire member 2b of the radiation source delivery wire 1' according to the second embodiment as in the first embodiment, pliability and flexibility of the distal end can be improved sufficiently. Further, because the irradiation member 3 is provided at the narrowing portion 22 of the operating wire member 2b, the diameter of the radiation source delivery wire 1 can be reduced and smoothness of the outside surface thereof can be improved.

FIG. 5 is a side view of a radiation source delivery wire according to a third embodiment of the present invention.

A radiation source delivery wire 10 shown in FIG. 5 comprises a flexible operating wire member 20 and an irradiation member 30 for applying radiation to a target tissue in a cavity of a living body as in the radiation source delivery wires 1 or 1' described with reference to FIGS. 1 to 4.

The operating wire member 20 is the same as the radiation source delivery wires 1 or 1' described with reference to FIGS. 1–4 except that it has no narrowing portion 22, as shown in FIG. 5.

The radiation source delivery wire 10 has an irradiation member 30 at a distal end thereof. The irradiation member 30 is constituted by a connected body which includes a plurality of independent or discrete radiation sources 301 connected in series along a common axial line by connectors 302.

Referring to FIGS. 6 and 7, each of the radiation sources 301 comprises a radiator or emitting member 301a and a covering layer 301b covering the outer periphery of the radiator 301a.

Although the configuration and shape of the radiation source 301 are not restricted to any particular ones, it is preferably a solid cylinder having a smaller outer diameter than the operating wire member 20. The radiator 301a can be formed by dissolving powder of a radioactive substance in an acid solution and impregnating porous particles such as glass and ceramic or water-absorptive gel with the acid solution as in the case of the radiators according to the first and second embodiments. Further, if the radioactive substance is liquid, the radiator may be formed by impregnating porous material or water absorptive gel with the liquid radioactive substance. Alternatively, if the radioactive substance is gaseous, the radiator may be formed by making the porous material absorb it. Further, it is possible to mix the radioactive substance-impregnated porous particles with a thermoplastic resin or silicone rubber, which may be shaped into a predetermined shape.

The covering layer 301b covers the entire outer periphery of the radiator 301a to seal or encapsulate the radioactive substance without being scattered. Therefore, the covering layer 301b is preferably formed of a material which has a strength capable of bearing a pressure, impact, vibration or the like from outside and is transparent for the radiation. Such a material includes for example, beryllium, aluminum, magnesium, titan, chrome, manganese, iron, cobalt, nickel, alloy thereof, metals such as stainless steel, polyethylene, polypropylene, polyamide, polyimide, fluororesin, and epoxy resin.

The length of each radiation source 301 in the axial direction is preferably as short as possible so as to reduce a radius of an entire curvature of the irradiation member 30 in order to increase ease with which it can pass through a tortuous path. The length is preferably 0.5 to 5.0 mm in viewpoints of ease of manufacturing, cost and the like, and more preferably 1.0 to 3.0 mm.

The individual radiation sources 301 are connected substantially in line on a common axial line by the connectors 302 so as to form a connected body. Preferably, each of the connectors 302 comprises a plurality of (two in the embodiment shown in FIG. 5) fine linear members or thin ribbon members 302a and 302b. The connector 302 transmits the motion of the operating wire member 20 to the irradiation member 30 and provides with a freedom for the irradiation member 30 to move freely bendably. Therefore, the connector is preferably formed of a material having appropriate stiffness, elasticity and flexibility. As such a material, the same material as that of the operating wire member 20 can be used. By forming the connector 302 of such a material, pliability and resilience are secured at the distal end of the radiation source delivery wire 1 so as to make it possible to send the wire through the path in the catheter smoothly.

Preferably, the linear members or ribbon members 302a and 302b of one connector 302 are respectively connected to an outer periphery of an end portion of the radiation source 301 at symmetrical positions by welding, bonding and the like. The linear members or ribbon members 302a, 302b of the connector 302 are shifted (preferably, 90°) in the circumferential direction relative to the adjacent connector.

A distal end 201 of the operating wire member 20 and a proximal end of the radiation source-connected body are connected substantially in line on an axial line of the operating wire member 20 by a second connector 303.

Incidentally, the length from the distal end of the most distal individual radiation source to the proximal end of the most proximal individual radiation source, i.e. the length of the connected body is preferably about 5 to 70 mm, more preferably about 10 to about 50 mm, most preferably about 20 to about 40 mm. The length of such a degree allows for sufficient radiation therapy.

The radiation source delivery wire 10 has the same length and outer diameter as the aforementioned radiation source delivery wires 1 or 1'.

In the third embodiment described above, like the first embodiment, preferably the distal end portion 201 of the operating wire member 20 is so constructed to form a narrowing portion whose diameter gradually decreases toward a distal end thereof. In this case, preferably, part of the narrowing portion may be covered with a coil. A proximal end portion of the coil may be fixed to the operating wire member 20, and a distal end portion thereof may be connected to a proximal end of the irradiation member 30.

Further, preferably, at least part of the irradiation member 30 and operating wire member 20 are covered with a thin-walled flexible sheath.

To manufacture the radiation source delivery wire 10, for example, first, a stainless pipe is cut at a predetermined length and an end thereof is closed by welding or the like. Then, a radiator or emitting member 301a produced preliminarily is inserted from the other end opening and the pipe is closed so as to complete the covering layer 301b and production of the radiation source 301.

Next, a Ni—Ti pipe having a predetermined diameter and thickness is mounted on a rotary fixing base and cut by irradiating laser beam from top of the side to produce a first connector 302.

The radiation sources 301 and the first connectors 302 are joined together by bonding, spot welding or the like by shifting their joints successively in the circumferential direction so as to produce the irradiation member 30 having a predetermined length.

Then, the distal end 201 of the operating wire member 20 is connected to the proximal end of the irradiation member 30 by bonding, spot welding or the like with a second connecting means 303.

With the above described manufacturing method, the radiation source delivery wire 10 shown in FIG. 5 can be obtained.

FIG. 8 is a side view of the radiation source delivery wire according to a fourth embodiment of the present invention. In FIG. 8, like reference numerals as in FIG. 5 denote like components or parts and a description thereof is omitted.

The radiation source delivery wire 10 shown in FIG. 8 is different from the third embodiment in that the irradiation member 30 comprises a connected body including a flexible, bendable tube-like member 40 which accommodates a plurality of individual radiation sources 301 substantially in line on a common axial line.

The tube-like member 40 is preferably capable of advancing through a tortuous cavity, and therefore it is formed of a material having appropriate stiffness and flexibility. Such a material includes, for example, metallic materials such as stainless steel and tungsten, superelastic alloy such as Ni—Ti alloy, Cu—Al—Ni alloy, Cu—Zn—Al alloy, Fe—Mn alloy, a resin such as polyamide, polyimide, polyethylene terephthalate, polybuthylene terephthalate, polyethylene, polypropylene, polyurethane and the like. Particularly the superelastic alloy is preferable. The tube-like member 40 can be made of rod, hollow pipe or ribbon wound in helical form. When the tube 40 is formed of a metallic material or a superelastic alloy, in particular, it is preferable to form an opening (slit) 401 by etching, laser production, electrical discharge machining or the like so as to be provided with flexibility. Preferably, the length of the opening 401 in the axial direction is substantially the same as that of the radiation source 301 in the axial direction. The tube-like member may be made of braid of thin wire.

Preferably, the distal end of the operating wire member 20 is inserted into the proximal end 402 of the tube-like member 40 so that the axial lines thereof are common and then connected to each other by bonding or welding. Preferably, a distal end 403 of the tube-like member 40 is rounded.

Preferably, radiopaque markers (not shown) made of radiopaque material are attached to the distal and proximal ends of the tube-like member 40.

The radiation sources 301 may be connected by bonding, welding or the like.

Because the radiation source delivery wire 10' of this embodiment includes the radiation source 301 in the tube-like member 40 produced integrally with the wire preliminarily, uniformity and integration in bending performance of the irradiation member 30 can be intensified, so that manufacturing and assembly are facilitated thereby leading to reduction of cost.

To produce the radiation source delivery wire 10', for example, first, Ni—Ti pipe having a thickness of about 100 micro meter and having an outer diameter slightly larger than those of the operating wire member 20 and radiation source 301 is cut to a predetermined length and mounted on a rotary fixing base. Then, laser beam is irradiated from top of the side so as to cut the pipe thereby producing the tube-like member 40 including a plurality of the openings 401. Then, the end of the tube-like member 40 is closed or narrowed. Next, the radiation source 301 is inserted into the interior of the tube-like member 40. The aforementioned tube-like member 40 and radiation source 301 may be fixed by bonding, welding or the like. After that, the distal end 201 of the operating wire member 20 is inserted into the proximal end 402 of the tube-like member 40 and then fixed by bonding, welding or the like. Finally, the radiopaque markers are attached to the distal end 403 and proximal end 42 of the tube-like member 40.

Figure 9:
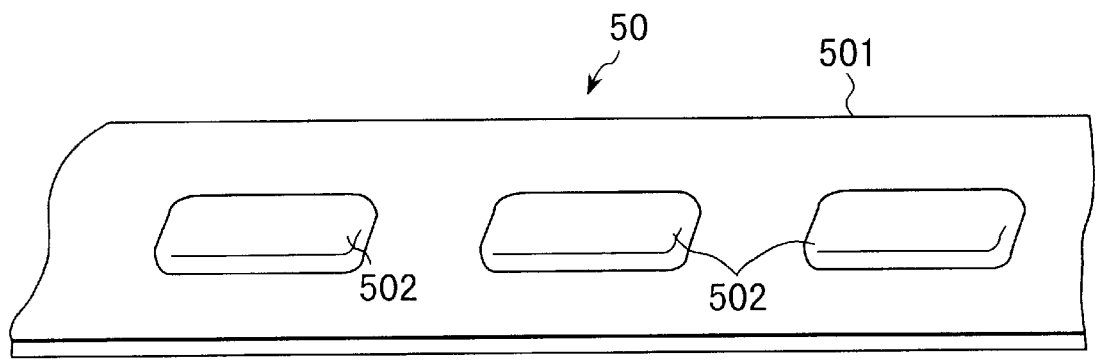
FIG. 9 is a oblique view showing the other irradiation member for use in a radiation dose delivery wire of the present invention.

FIG. 9 shows another embodiment of the irradiation member of the radiation source delivery wire of the present invention. This irradiation member 50 comprises a flexible, bendable belt-like (ribbon) substrate 501 and a plurality of radiation sources 502 fixed thereon including a radioactive substance. The radiation sources 502 are spaced apart from each other in the axial direction of the ribbon substrate. The radiation source 502 may be prepared by mixing powdery radioactive substance in a flexible medium such as a thermoplastic resin or silicone rubber and coating the mixture on the substrate 501. Alternatively, the radiation source may prepared by mixing porous particles supporting a radioactive substance with the flexible medium mentioned above and coating the mixture on the substrate 501. The ribbon substrate 501 is preferably formed of a metallic material such as stainless steel, or a superelastic alloy described earlier.

Figure 10:
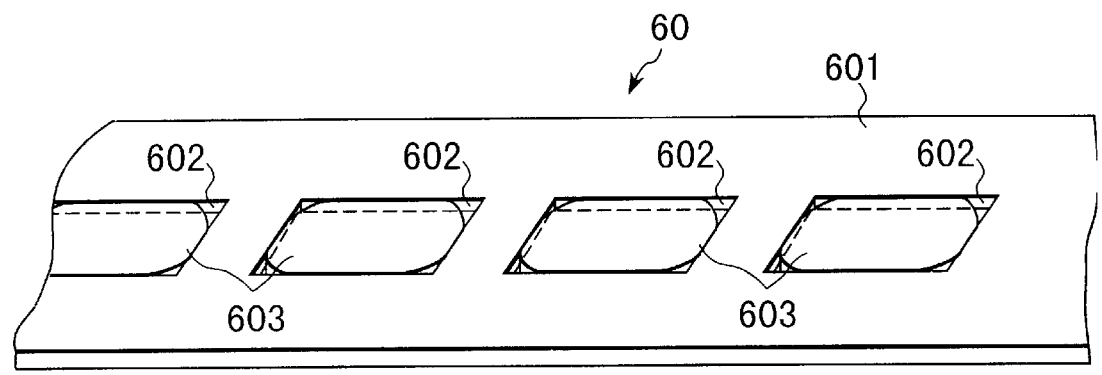
FIG. 10 is a oblique view showing a further irradiation member for use in a radiation dose delivery wire of the present invention.

FIG. 10 shows other embodiment of the irradiation member of the radiation source delivery wire of the present invention. This irradiation member 60 includes a flexible, bendable belt-like (ribbon) substrate 601 having a plurality of through holes 602. A plurality of individual radiation sources 602 including a radioactive substance, such as the individual radiation source 301 described in the third embodiment, are fixed within through holes 602, respectively. The ribbon substrate 601 is preferably formed of the same material as the ribbon substrate 501 described with reference to FIG. 9.

Next, a radiation therapy catheter assembly suitable for use with the radiation source delivery wire of the present invention will be described with reference to the accompanying drawings.

FIG. 11 is a longitudinal sectional view showing a first embodiment of the radiation therapy catheter assembly of the present invention. The radiation therapy catheter assembly 100 of the present invention shown in FIG. 11 comprises a radiation therapy catheter 101 and a radiation source delivery wire 107 (for example, a radiation source delivery wire explained with reference to FIGS. 1 to 10) of the present invention.

According to this embodiment, the radiation therapy catheter 101 is intended to be inserted into a cavity of a living body, such as blood vessel, for radiation therapy. The catheter 101 comprises a catheter body 110 guided by a guide wire 108 in the cavity, an elongated lumen (radiation wire lumen) 102 which is provided in the catheter body 110 and through which the radiation source delivery wire 107 can be inserted, radiopaque markers 105a and 105b for identifying a position of the radiation source 106 of the radiation source delivery wire 107, and an elongated lumen (guide wire lumen) 104 through which the guide wire 108 can be inserted.

The catheter body 110 is formed of a flexible material. To ensure easiness of operation and safety in introducing the catheter up to a target portion through a guiding catheter or a cavity of a living body such as blood vessel, preferably the catheter is formed of a material having appropriate pliability, elasticity, sliding performance, mechanical strength and anti-kink performance. The material of the catheter body 110 includes, for example, polyolefin such as polyethylene and polypropylene, ethylene-vinyl acetate copolymer, polyvinyl chloride, polyester such as polyethylene terephthalate and polybutylene terephthalate, polyamide, polyimide, polyurethane, fluororesin, elastomer and copolymer thereof, polymer alloy, and combinations of two or more thereof.

To prevent the radiation emitted from the radiation source 106, which is moving through the catheter body 110 when the radiation source delivery wire 107 is inserted or removed, from irradiating a tissue other than the target portion, preferably, powder of a material (radiation shielding material) which hardly transmits the radiation therethrough, e.g., a heavy metal such as Au, Ag, Pt, Pb and W, barium sulfate, bismuth oxide, is mixed in the material forming the catheter body 110. However, it is necessary to avoid mixing of any of the radiation shielding materials in a portion for carrying out radiation therapy, i.e., in a region between the radiopaque markers 105a and 105b of the catheter body 110.

Further, to improve the slidability of the radiation therapy catheter 101, it is possible to cover an outside surface of the catheter body 110 with a hydrophilic polymeric material exhibiting lubricity in wet condition.

Although a length of the catheter body 110 is selected appropriately depending on a case to which it is applied, preferably it is 0.5 to 2 mm and more preferably 1.0 to 1.5 mm. An outer diameter thereof is preferably 0.5 to 5 mm and more preferably 0.8 to 3.0 mm.

The radiation wire lumen 102 formed inside the catheter body 110 has its distal end closed, constituting a closed end 121. The closed end 121 prevents body fluid such as blood from making contact with the radiation source 106 via the lumen or the radioactive substance from leaking into the living body.

The radiation wire lumen 102 is provided coaxially with the catheter body 110. Consequently, the positioning of the radiation source 106 along the axis of the catheter body 110 is facilitated. Therefore, a distance from the radiation source 106 to an inner wall of a cavity of a living body at which radiation is to be directed can be substantially equalized so that a dose of radiation to the target tissue becomes uniform.

The guide wire lumen 104 is provided at a further distal end side of the closed end 121 of the radiation wire lumen 102. The guide wire lumen 104 is an elongated lumen through which the guide wire 108 is inserted for guiding the radiation therapy catheter 101 into the cavity of a living body. The lumen 104 has a proximal end opening 142 at the side of the catheter 110 and a distal end opening 141 substantially in the center of the distal end of the catheter body 110. By providing the distal end opening 142 on the side of the catheter body 110, the guide wire can be pulled out or replaced rapidly, thereby ensuring excellent operability and handling.

The guide wire lumen 104 is provided coaxially with the catheter body 110. As a result, the catheter body 110 introduced by the guide wire 108 can be moved safely and smoothly.

The guide wire lumen 104 and radiation wire lumen 102 are arranged coaxially. With such a structure, the radiation source 106 is easy to be located in the center of the living body cavity so that irradiation of the radiation can be done equally or uniformly.

Further, by providing the radiation wire lumen 102 and guide wire lumen 104 coaxially, the catheter body 110 can be so constructed as if it includes only a single cavity in the radial direction, so that reduction of the diameter of the whole catheter body 110 can be achieved. Therefore, this is applicable for radiation therapy in a narrow cavity, so that the scope of application is expanded and the safety and accuracy are improved.

The radiopaque markers 105a and 105b are provided on an outer periphery in the vicinity of the distal end of the catheter body 110. As a result, the radiation therapy catheter 101 can be located accurately at a target portion and a position of the radiation source 106 can be detected accurately.

The radiopaque markers 105a and 105b are formed of a radiopaque material. Because the markers are visible from outside under radiation fluoroscopy, the position of the markers can be recognized and determined. Thus, the radiation therapy catheter 101 can be positioned easily and accurately at a desired position, so that the radiation source 106 can be disposed at a target portion.

The radiopaque material for forming the radiopaque markers 105a and 105b includes, for example, heavy metals such as Au, Ag, Pt, W, Pb, and alloys and salts thereof.

The radiopaque markers 105a are 105b are constituted by a thin-walled tube-like members and fixed by caulking the tube-like members onto an outer peripheral surface of the catheter body 110. In this case, preferably, an inner diameter of the radiopaque markers 105a and 105b is substantially equal to or slightly smaller than an outer diameter of the catheter body 110. The configuration of the radiopaque markers is not restricted to the tube shown in FIG. 10, but may be ribbon member, linear member or the like.

According to this embodiment, part of the radiopaque markers 105a and 105b are embedded in the outer peripheral surface region of the catheter body 110 such that they are fixed securely. Further, the radiopaque markers 105a and 105b are covered with a resin 111. As a result, the fixing of the catheter body 110 is secured, and steps between the outer peripheral surface of the catheter body 110 and radiopaque markers 105a are 105b are eliminated so as to ensure smooth sliding of the catheter body 110 in the lumen and preventing a damage to the tissue. With such a construction, the radiopaque markers 105a and 105b are not shifted or doe not drop due to bending or the like of the catheter body 110 so as to achieve the function of identifying the position of the radiation source 106 accurately.

The resin 111 is not restricted to any particular one. The resin may be any resin for forming the catheter body 110, and is preferably the same as the catheter body-forming resin material. This resin 111 may be applied by coating a solution containing the resin 111 around the radiopaque markers 105a and 105b so as to fill the stepped portion formed with the catheter body 110.

Preferably, the radiopaque markers 105a and 105b are disposed at substantially the same interval as a length of the radiation source 106 in the axial direction. As a result, the position of the radiation source 106 and an irradiation range of radiation can be identified accurately. According to this embodiment, if the distal end of the radiation source 106 is set at the proximal end of the radiopaque marker 105a, the proximal end of the radiation source 106 corresponds to the distal end of the radiopaque marker 105b.

The radiopaque marker of the radiation therapy catheter should not be limited to the form shown in the figure, but it suffices for the radiopaque maker to be constituted such that a predetermined region of the distal end side portion of the catheter can be positioned near the target tissue in a living body owing to the marker. Thus, for example, only one radiopaque marker may be provided on the catheter.

In case where a radiation source delivery wire having no radiopaque marker is used, when the radiation source delivery wire is inserted until a distal end thereof abuts against the closed end 121 of the radiation wire lumen 102, preferably the radiation source 106 is located in a predetermined region of the catheter (for example, the region between the radiopaque markers 105a and 105b). As a result, even in the radiation source delivery wire 107 having no radiopaque markers, the position of the radiation source 106 can be identified.

A connector 130 whose inner diameter gradually increases toward the proximal end is attached to the proximal end of the catheter body 110. The distal end of the connector 130 is connected to the radiation wire lumen 102, so that the radiation source delivery wire 107 can be inserted into the radiation wire lumen 102 from the connector 130. On the other hand, the proximal end of the connector 130 is so constructed as to be connectable to an after-loader (not shown) capable of sending, winding or accommodating the radiation source delivery wire 107. The connector 130 may be formed of various kinds of resins, preferably, for example, polyethylene, polypropylene, polycarbonate, polyamide, polysulfone, polyarylate or the like.

The radiation source delivery wire 107 of the present invention includes a radiation source 106 in the vicinity of the distal end. The radiopaque markers 161 (corresponds to the markers 5a and 5b of FIG. 1) are provided on both ends of the radiation source 106. The markers make it possible to visually identify the position of the radiation source 106 directly, as described above. Therefore, the position of the radiation source 106 can be recognized more easily and accurately owing to the presence of the markers 161 together with the markers 105a and 105b like the radiopaque markers 105a, 105b provided on the catheter 101 of the present invention. It is possible to fix a ring made of radiopaque material around an outer periphery of the radiation source delivery wire 107 in the vicinity of both ends of the radiation source 106 by caulking to provide the marker 161.

The radiation therapy catheter 101 may be manufactured in the following method.

First, a tube for the catheter body is formed by extrusion. This tube is cut to an appropriate length to produce the catheter body 110.

The radiopaque markers 105a, 105b of ring shape produced preliminarily are fitted around the outer periphery of the catheter body 110.

If an inner diameter of the rings of the radiopaque markers 105a, 105b is smaller than the outer diameter of the catheter body 110, the catheter body 110 is inserted into each ring in a condition that it is stretched and then the stretching condition is released. Further, the rings and catheter body are heated so that part or all thereof is embedded into the outer peripheral surface region of the catheter body 110. The resin 111 is applied thereon so as to fill the stepped portion formed with the radiopaque markers 105a and 105b and catheter body 110.

Next, filler made of the same resin material as the catheter body 110 is injected through the distal end opening 141 of the catheter body 110, and the portion from the distal portion with respect to the radiopaque marker 105a up to the distal end opening 141 is closed. As a result, the radiation wire lumen 102 having the closed end 121 is formed.

Further, the side opening 142 of the guide wire lumen 104 is formed on a side wall of the catheter body 110 at a proximal portion of the catheter body 110 with respect to the closed end 121. Further, a core made of a metal having substantially the same outer diameter as the inner diameter of the guide wire lumen 104 is inserted from the distal end opening 141 of the catheter body 110 up to a position which communicates with the proximal end opening 142. By bringing the distal end of the catheter body 110 in a bottomed cylindrical heated die in this state, the guide wire lumen 104 is formed and the distal end of the catheter body 110 is rounded.

On the other hand, a connector 130 is attached to the proximal end of the catheter body 110 and both of them are fixed with an adhesive so as to produce the radiation therapy catheter 101.

If a covering layer made of a hydrophilic resin is formed on the surface of the catheter body 110, first, a supporting metallic rod is inserted into the radiation wire lumen 102 from the proximal end and further, another supporting metallic rod is inserted also into the guide wire lumen 104 from the distal end opening 141 or proximal end opening 142, and the catheter body 110 is dipped in a resin solution from a distal end thereof.

Next, as an example of radiation therapy using the radiation therapy catheter assembly of this embodiment, a case of treatment on PTCA underwent portion (blood vessel stenosis portion) will be described.

First, a sheath is inserted into a femoral artery, and then a guiding catheter (not shown) is inserted through the sheath and the distal end of the guiding catheter is located this side in the vicinity of a target tissue (blood vessel stenosis portion which has subjected to PTCA).

Next, while sending the guide wire 108 in advance, the radiation therapy catheter 101 is inserted into the guiding catheter. Usually, it is preferred to use the guiding catheter and guide wire which have been used for guiding a balloon dilating catheter for treating stenosis, after removing the balloon dilating catheter. Then, a contrast medium is poured from the inside of the guiding catheter so as to recognize the position of the target tissue, and while confirming the positions of the radiopaque markers 105a and 105b under X-ray fluoroscopy, the radiation therapy catheter 101 is advanced in the distal direction to position the radiation therapy catheter 101 so that its portion between the markers 105a and 105b is located in the vicinity of the target tissue.

Thereafter, the radiation source delivery wire 107 is inserted into the radiation wire lumen 102 and advanced so that the radiation source 106 is located between the radiopaque markers 105a and 105b.

If the radiation source 106 reaches the target position (see FIG. 11), it is kept in the target position for a predetermined time to irradiate the target tissue with the radiation from the radiation source 106.

After the irradiation of radiation is completed, the radiation source delivery wire 107 is pulled out rapidly and accommodated in a shielded container.

FIG. 12 is a longitudinal sectional view showing a second embodiment of a radiation therapy catheter assembly of the present invention. Like reference numerals denotes like components or parts as in FIG. 11 and a description thereof is omitted.

The radiation therapy catheter assembly 100 of this embodiment comprises the radiation therapy catheter 101 and the radiation source delivery wire 107 of the present invention.

In the radiation therapy catheter 101, the guide wire lumen 104 and the radiation wire lumen 102 are provided in parallel in the axial direction. At the proximal end side of the proximal end opening 142 of the guide wire lumen 104, a fluid passage lumen 145 constituting a path for injecting or sucking a liquid or for sucking a body fluid. A side hole 146 is provided near a distal end thereof.

The connector 130 is attached to a distal end of the radiation therapy catheter 101. The connector 130 is a hollow member branched into two pipes. One branch pipe constitutes a port 147 communicating with the radiation wire lumen 102, and the other branch pipe constitutes a port 144 communicating with the fluid passage lumen 145.

This embodiment is different from the first embodiment of the catheter assembly in that the radiopaque markers 105a and 105b are provided inside the catheter body 110. Because smoothness of the outer periphery of the catheter body 110 is maintained with this structure, the operability and safety of the catheter body 110 in a cavity of a living body are improved.

The radiopaque markers 105a and 105b are provided outside the radiation wire lumen 102. Because, with such a structure, the radiopaque markers 105a and 105b can be placed near the radiation source 106, a position of the radiation source 106 can be detected more accurately. For example, if the catheter body 110 and the radiation source delivery wire 107 are bent near a position in which the radiation source 106 is located, the relative position is hardly shifted so that the position of the radiation source 106 can be always detected accurately.

The radiation therapy catheter 101 of this embodiment can be manufactured, for example, in the following manner.

As in the first embodiment of the catheter assembly, a tube having a single cavity for forming the catheter body 101 is formed by extrusion. Next, a core for preventing a clogging is placed inside the tube and the radiopaque markers 105a and 105b are placed at predetermined positions in the tube. Then, the tube is inserted into an extrusion die so as to form a single lumen in which the guide wire lumen 104 communicates with the fluid passage lumen 145 in parallel to the center lumen providing the radiation wire lumen 102.

Next, by closing the distal end of the tube, the closed end 121 is formed for the center lumen 102.

Then, by injecting a filler made of a resin the same as the resin forming the catheter body 110 into a portion apart by a predetermined distance from the distal end of the lumen which will serve for a guide wire lumen toward the distal end, the lumen is divided so that the distal end side thereof serves as the guide wire lumen 104 and the proximal end side serves as the fluid passage lumen 145. The proximal end opening 142 is provided at the proximal end of the guide wire lumen 104 and the side hole 146 is provided near the distal end of the fluid passage lumen 145.

In the radiation therapy catheter 101 of this embodiment, the position of the proximal end opening 142 of the guide wire lumen 104 can be selected and provided more freely than the first embodiment. Although according to the first embodiment of the catheter assembly, the proximal end opening 142 of the guide wire lumen 104 is restricted to distal end side relative to the closed end 121 of the radiation wire lumen 102, there is no such a restriction in this embodiment and the position of the proximal end opening 142 can be set arbitrarily depending on the operability, irradiation portion and the like of the guide wire 108.

Further, because the side hole 146 of the fluid passage lumen 145 can be provided at any place, for example, contrast medium or the like can be thrown in directly from the vicinity of the target tissue, thereby contributing largely to improvement of diagnostic accuracy and therapy effect.

As in the first embodiment of the catheter assembly, it is possible to form the distal end of the catheter body 110 in a round shape and form the covering layer made of a hydrophilic resin on the surface of the catheter body 110. Further, by attaching the connector 130 to the distal end of the catheter body 110 and fixing it with an adhesive, the radiation therapy catheter 101 is obtained.

According to this embodiment, the radiation wire lumen 102 is disposed coaxially with the catheter body 110. The radiation therapy catheter of the present invention is not restricted to this type, but it is possible to dispose the radiation wire lumen 102 at a position shifted relative to a lateral section of the catheter body 110. However, if the radiation wire lumen 102 is disposed coaxially with the catheter body 110 as in this embodiment, it is easy to place the radiation source in the center of a cavity of a living body, such as a blood vessel, so that uniform irradiation of radiation is enabled.

Figure 13:
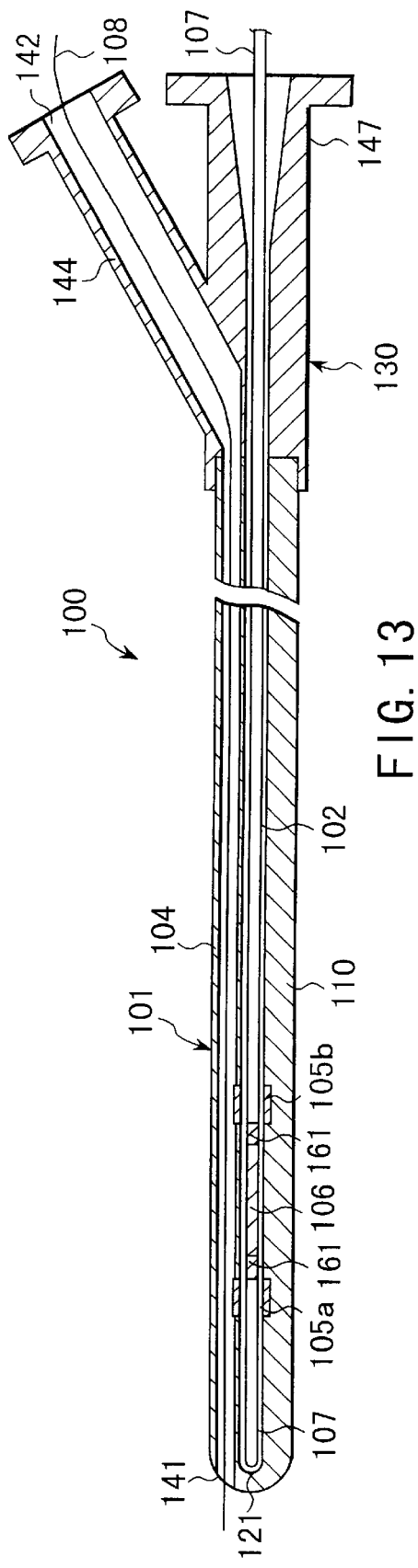
FIG. 13 is a longitudinal sectional view showing the third embodiment of catheter assembly for radiation therapy of the present invention.

FIG. 13 is a longitudinal sectional view showing a third embodiment of the radiation therapy catheter assembly of the present invention. This embodiment is equal to the radiation therapy catheter assembly shown in FIG. 12 except that the guide wire lumen 104 extends up to the proximal end, the proximal end opening 142 is located at the proximal end of the port 144.

The guide wire lumen 104 can be made to function as the fluid passage cavity in such a condition that the guide wire 108 is not inserted through. With such a structure, a necessity of providing the catheter body with the side hole is eliminated, thereby simplifying a manufacturing process of the catheter body.

Figure 14:
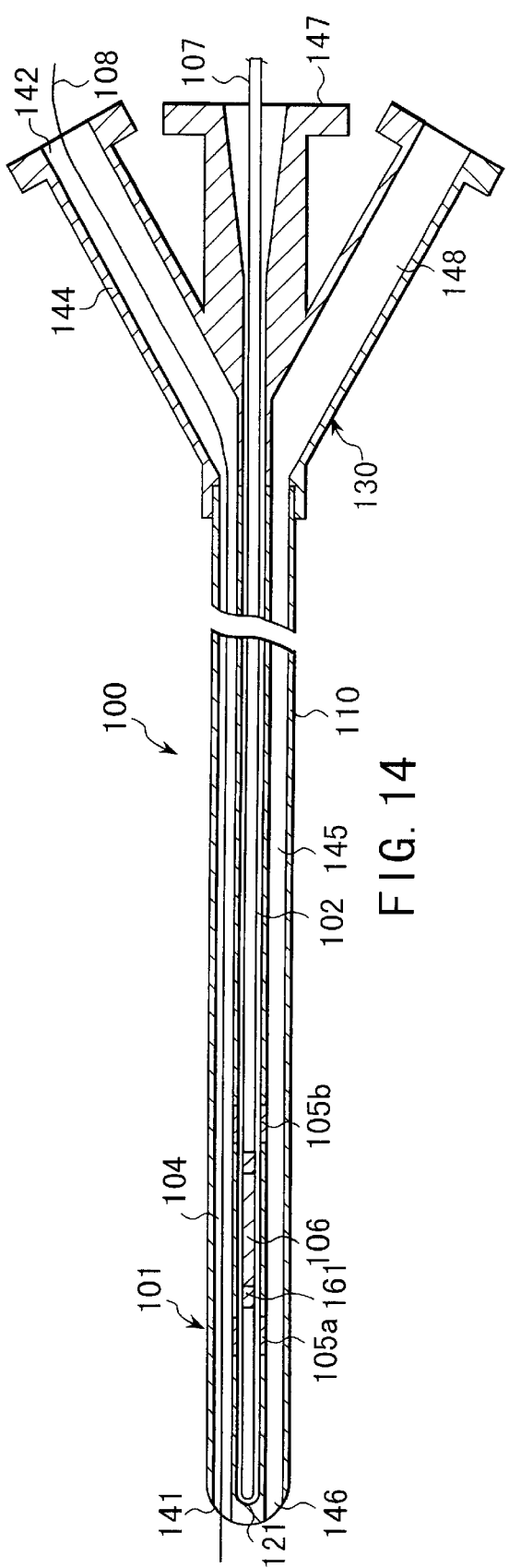
FIG. 14 is a longitudinal sectional view showing the fourth embodiment of catheter assembly for radiation therapy of the present invention.

FIG. 14 is a longitudinal sectional view showing a fourth embodiment of the radiation therapy catheter assembly of the present invention.

According to this embodiment, three elongated lumens, i.e., the guide wire lumen 104, fluid passage lumen 145 and radiation wire lumen 102 are provided in parallel in the axial direction of the catheter body 110.

The connector 130 is attached to the proximal end of the radiation therapy catheter 101. The connector 130 is a hollow member having three branch pipes and those branch pipes constitute a port 147 communicating with the radiation wire lumen 102, a port 148 communicating with the fluid passage lumen 145 and a port 144 communicating with the guide wire lumen 104.

The radiation therapy catheter 101 of this embodiment is equal to the radiation therapy catheter shown in FIG. 13 except that the guide wire lumen 104 and fluid passage lumen 145 are provided independently of each other.

Although the respective embodiments of the radiation source delivery wire and radiation therapy catheter assembly of the present invention have been described above, the present invention is not restricted to these embodiments. For example, it is possible to fix a lubricating substance such as a hydrophilic polymeric substance on the surface of the radiation source delivery wire 1. Further, instead of the tube-like connecting means shown in FIG. 8, a plurality of radiation sources arranged substantially in line on a common axial line may be connected by bonding one or more linear members or spot-welding on the outer peripheral surface of those radiation sources. As for the catheter assembly, for example, the guide wire lumen may be provided in a tube provided on the outer periphery of the catheter body as well as inside the catheter body. Further, a structure of each means may be replaced with any structure having the same function.

As described above, because the radiation source delivery wire of the present invention is so constructed that the irradiation member including the radiation source is entirely flexible and bendable, it can be inserted smoothly with the safety through a complicatedly curved catheter or cavity of a living body. Further, if the operating wire member has the narrowing portion which gradually narrows toward the distal end thereof, flexibility of the distal end is further improved.

Such a radiation source delivery wire can be used widely for radiation therapy in the lumens such as the hepatic artery, marginal artery, veins, respiratory system, bile duct, prostate.

The radiation therapy catheter assembly of the present invention makes it possible to carry out diagnosis, treatment and the like rapidly and securely to detect a position of the radiation source accurately. As a result, the safety and effect of the irradiation are improved thereby reducing danger of side effect and recurrence of disease symptom. Further, because the radiation therapy catheter of the present invention is provided with a radiopaque marker, this is available even if the radiation source delivery wire has no marker. Further, if the radiation source delivery wire having the markers is used, a further secure detection of the radiation source is enabled.

Additional advantages and modifications will readily occur to those skilled in the art. Therefore, the invention in its broader aspect is not limited to the specific details and representative embodiments shown and described herein. Accordingly, various modifications may be made without departing from the spirit or scope of the general inventive concept as defined by the appended claims and their equivalents.

What is claimed is:

1. A radiation source delivery wire comprising:
a flexible operating wire member having a distal end portion constituting a narrowing portion which gradually narrows toward a distal end, said operating wire member having a stiffness capable of transmitting an operation at its proximal end to its distal end;
a covering layer provided on an external surface of said operating wire member, said covering layer providing said operating member with resilience and pliability;
an irradiation member including a radiation source for applying radiation to a target portion in a cavity of a living body, said irradiation member being so constructed as to be flexibly bendable; and
a tube made of a flexible resin material directly fitted to said irradiation member to sealingly encapsulate said irradiation member, a proximal end of said tube being joined to said covering layer to constitute a smooth surface of the radiation source delivery wire.

2. The delivery wire according to claim 1, wherein said irradiation member is provided at the narrowing portion.

3. The delivery wire according to claim 1, wherein said irradiation member includes radiopaque markers for indicating a position of the radiation source.

4. The delivery wire according to claim 3, wherein said radiation source and radiopaque markers are accommodated in a thin-walled flexible tube.

5. The delivery wire according to claim 4, wherein at least one end of said tube is closed.

6. The delivery wire according to claim 4, wherein said tube is formed of a resin.

7. The delivery wire according to claim 1, wherein said radiation source comprises a β-emitting radio-isotope.

8. The delivery wire according to claim 1, wherein said radiation source comprises a powdery emitting member.

9. The delivery wire according to claim 1, wherein said radiation source comprises a deformable substrate and radioactive substance carried by said substrate.

10. The delivery wire according to claim 1, wherein said irradiation member comprises a plurality of individual radiation sources, and flexible connectors for connecting said plurality of the individual radiation sources substantially in line on a common axial line.

11. The delivery wire according to claim 10, wherein each of said connectors is provided between two adjacent individual radiation sources and comprises a plurality of linear members or ribbon members whose one end is connected to a proximal end of one of the two adjacent individual radiation sources and whose other end is connected to a distal end of the other of the two adjacent individual radiation sources.

12. The delivery wire according to claim 10, wherein said connector is made of a flexible, bendable tube-like member accommodating said plurality of the individual radiation sources substantially in line on the common axial line.

13. A radiation source delivery wire comprising:
a flexible operating wire member; and
an irradiation member comprising a flexible, deformable medium and a radioactive substance mixed in or carried by said medium for applying radiation to a target in a cavity of a living body,
wherein said flexible, deformable medium is formed of a material selected from the group consisting of a soft rubber material, elastic resin material and waterproof gel.

14. The delivery wire according to claim 13, wherein said irradiation member is accommodated in a thin-walled, flexible tube.

15. The delivery wire according to claim 14, wherein at least one end of the tube is closed.

16. The delivery wire according to claim 14, wherein said tube is formed of a resin.

17. The delivery wire according to claim 13, wherein said irradiation member is accommodated in a thin-walled, flexible tube, and at least one end of the tube is closed by a radiopaque marker.

18. The delivery wire according to claim 13, wherein said radiation source contains a β-emitting radio-isotope.

19. A radiation source delivery wire comprising:
a flexible operating wire member having a stiffness capable of transmitting an operation at its proximal end to its distal end; and
an irradiation member for applying radiation to a target portion in a cavity of a living body,
wherein said irradiation member comprises a connected body including a plurality of individual radiation sources and flexibly bendable connectors connecting said individual radiation sources substantially in line on a common axial line; and a joint portion joining a proximal end of the connected body to a distal end of the operating wire member, and wherein the connected body is provided more distal than the distal end of the operating wire member.

20. The delivery wire according to claim 19, wherein said connected body has a length of about 20 to about 40 mm.

21. The delivery wire according to claim 19, wherein said connector is provided between two adjacent individual emitting members and comprises a plurality of linear members or ribbon members whose one end is connected to a proximal end of one of the adjacent emitting members and whose other end is connected to a distal end of the other of the adjacent radiators.

22. The delivery wire according to claim 21, wherein said connector comprises a plurality of connecting members comprising a plurality of linear members or ribbon members provided between two adjacent emitting members, and the connecting members are shifted in a circumferential direction of the emitting member relative to the other.

23. The delivery wire according to claim 19, wherein said connector is a substantially tube-like, flexibly bendable member located outside said plurality of the emitting members, and accommodates said plurality of the emitting members substantially in line on a common axial line.

24. A catheter assembly for radiation therapy comprising:
(a) a radiation source delivery wire according to claim 1;
(b) a catheter for radiation therapy, comprising a catheter body, and an elongated lumen which is provided in the catheter body and through which the radiation source delivery wire may be inserted.

25. The assembly according to claim 24, wherein said catheter has a radiopaque marker disposed in the catheter body, for indicating a position of the radiation source of the wire device inserted into said lumen.

26. The assembly according to claim 25, wherein said radiopaque marker is formed of X-ray opaque material.

27. The assembly according to claim 24, wherein a distal end of the cavity is closed.

28. A radiation source delivery wire comprising:
a flexible operating wire member having a distal end portion constituting a narrowing portion which gradually narrows toward a distal end, said operating wire member having a stiffness capable of transmitting an operation at its proximal end to its distal end;
an irradiation member including a radiation source for applying radiation to a target portion in a cavity of a living body, said irradiation member being so constructed as to be flexibly bendable; and
a tube made of a flexible resin material directly fitted to said irradiation member to sealingly encapsulating said irradiation member; and
a fixing member filling a space between said tube and said narrowing portion of the operating wire member to fix said irradiation member and said operating wire member.

29. A radiation therapy method comprising:
providing a radiation therapy catheter comprising a catheter body, an elongated lumen which is provided in the catheter body and through which a radiation source delivery wire can be inserted, and a radiopaque marker provided for indicating a predetermine region at a distal portion of the catheter;
positioning said radiation therapy catheter such that said radiopaque marker is positioned in the vicinity of a target tissue of a living body;
inserting a radiation source delivery wire according to claim 1 or 28 into said lumen of said catheter, and positioning said radiation source in the predetermined region while referring to the radiopaque markers;
keeping the radiation source to said predetermined region for a predetermined time so as to administer the prescribed dose of radiation to the target tissue for a predetermined time; and
removing the radiation source delivery wire from the living body.

30. A radiation therapy method comprising:
providing a catheter assembly for radiation therapy, comprising, in combination:
a radiation therapy catheter comprising a catheter body, and an elongated lumen having a closed distal end, and an elongated lumen having a closed distal end, which is provided in the catheter body and through which a radiation source delivery wire can be inserted, and
a radiation source delivery wire according to claim 1 or 28,
said catheter and wire device being constructed such that when said wire device is inserted into said elongated lumen until its distal end reaches said closed distal end of said elongated lumen, the radiation source of said wire device is located in a predetermined distal region of said catheter;
positioning said catheter such that said predetermined region is located in the vicinity of a target tissue in a living body;
inserting the radiation source delivery wire according to claim 1 or 28 into said elongated lumen until its distal end reaches said closed end of said elongated lumen so that the radiation source is located in said predetermined region;
keeping the radiation source to said predetermined region for a predetermined time so as to administer the prescribed dose of radiation to a target tissue for a predetermined time; and
removing the radiation source delivery wire from the living body.

31. The delivery wire according to claim 30, wherein said irradiation member is provided at the narrowing portion.

32. The delivery wire according to claim 30, wherein said irradiation member includes radiopaque markers for indicating a position of the radiation source.

33. The delivery wire according to claim 32, wherein said radiation source and radiopaque markers are accommodated in a thin-walled flexible tube.

34. The delivery wire according to claim 33, wherein at least one end of said tube is closed.

35. The delivery wire according to claim 33, wherein said tube is formed of a resin.

36. The delivery wire according to claim 30, wherein said radiation source comprises a β-emitting radio-isotope.

37. The delivery wire according to claim 30, wherein said radiation source comprises a powdery emitting member.

38. The delivery wire according to claim 30, wherein said radiation source comprises a deformable substrate and radioactive substance carried by said substrate.

39. The delivery wire according to claim 30, wherein said irradiation member comprises a plurality of individual radiation sources, and flexible connectors for connecting said plurality of individual radiation sources substantially in line on a common axial line.

40. The delivery wire according to claim 39, wherein each of said connectors is provided between two adjacent individual radiation sources and comprises a plurality of linear members or ribbon members having one end connected to a proximal end of one of the two adjacent individual radiation sources and having another end connected to a distal end of the other end of the two adjacent individual radiation sources.

41. The delivery wire according to claim 39, wherein said connector is made of a flexible, bendable tube-like member accommodating said plurality of individual radiation sources substantially in line on the common axial line.

* * * * *